US008506164B2

(12) United States Patent
Lecointe

(10) Patent No.: US 8,506,164 B2
(45) Date of Patent: Aug. 13, 2013

(54) BAG FOR PACKAGING A BIOLOGICAL SUBSTANCE COMPRISING OPENINGS FOR HANGING TO A SUPPORT DEVICE, AND STRIP FORMED WITH SUCH BAGS

(75) Inventor: Pascal Lecointe, Saint Gregoire (FR)

(73) Assignee: IMV Technologies, L'Aigle (FR)

( * ) Notice: Subject to any disclaimer, the term of this patent is extended or adjusted under 35 U.S.C. 154(b) by 357 days.

(21) Appl. No.: 12/512,332

(22) Filed: Jul. 30, 2009

(65) Prior Publication Data

US 2010/0027916 A1 Feb. 4, 2010

(30) Foreign Application Priority Data

Jul. 31, 2008 (FR) ..................................... 08 55292

(51) Int. Cl.
*B65D 33/10* (2006.01)
*B65D 33/14* (2006.01)
*A61B 19/00* (2006.01)
*A61M 5/32* (2006.01)

(52) U.S. Cl.
USPC ................. 383/9; 383/22; 604/403; 604/404; 604/405; 604/406; 604/407; 604/408; 604/409; 604/410; 604/411; 604/412; 604/413; 604/414; 604/415; 604/416

(58) Field of Classification Search
USPC ............................... 383/9, 22; 604/403–416
IPC ....................................................... B65D 77/28
See application file for complete search history.

(56) References Cited

U.S. PATENT DOCUMENTS

| | | | | | |
|---|---|---|---|---|---|
| 4,270,533 | A | * | 6/1981 | Andreas | 604/142 |
| 4,278,198 | A | * | 7/1981 | Norton et al. | 383/119 |
| 4,368,765 | A | * | 1/1983 | Larkin et al. | 604/408 |
| 4,883,450 | A | * | 11/1989 | Benoit | 493/196 |
| 4,887,913 | A | * | 12/1989 | Sengewald | 383/96 |
| 5,100,564 | A | | 3/1992 | Pall et al. | |
| 5,207,328 | A | * | 5/1993 | Bose et al. | 206/554 |
| 5,664,399 | A | * | 9/1997 | Cassou | 53/284.7 |
| 2003/0053938 | A1 | * | 3/2003 | Szeles | 422/102 |
| 2003/0191005 | A1 | * | 10/2003 | Coelho et al. | 494/37 |
| 2006/0068369 | A1 | | 3/2006 | Coelho et al. | |
| 2006/0215941 | A1 | * | 9/2006 | Golbert | 383/8 |
| 2008/0277308 | A1 | * | 11/2008 | Simhaee | 206/554 |

FOREIGN PATENT DOCUMENTS

| | | | |
|---|---|---|---|
| EP | 1 317 224 | A | 6/2003 |
| EP | 1 609 495 | A | 12/2005 |

* cited by examiner

*Primary Examiner* — Nathan J Newhouse
*Assistant Examiner* — Derek Battisti
(74) *Attorney, Agent, or Firm* — Pauley Petersen & Erickson

(57) ABSTRACT

The present invention relates to a bag (1) for packaging a biological substance, such as animal semen, which is formed by two plastic walls (10, 11) assembled so as to define a pouch (P) for receiving said substance and that comprises a line (15) communicating with said pouch (P) a line for filling the same, this bag comprising in addition at least one pair of openings (3, 4) located on both sides of said line (15), in order to get hung, via these openings, to fingers that are complementary to a supporting device.

This bag is characterized in that at least one of these openings (3, 4) has an oblong shape, extends perpendicularly to said line (15), and comprises an area forming a hard spot.

The invention relates also to a strip formed by juxtaposing such bags (1), and an assembly comprised of a bag and a hanging support.

9 Claims, 3 Drawing Sheets

FIG. 5a
FIG. 5b
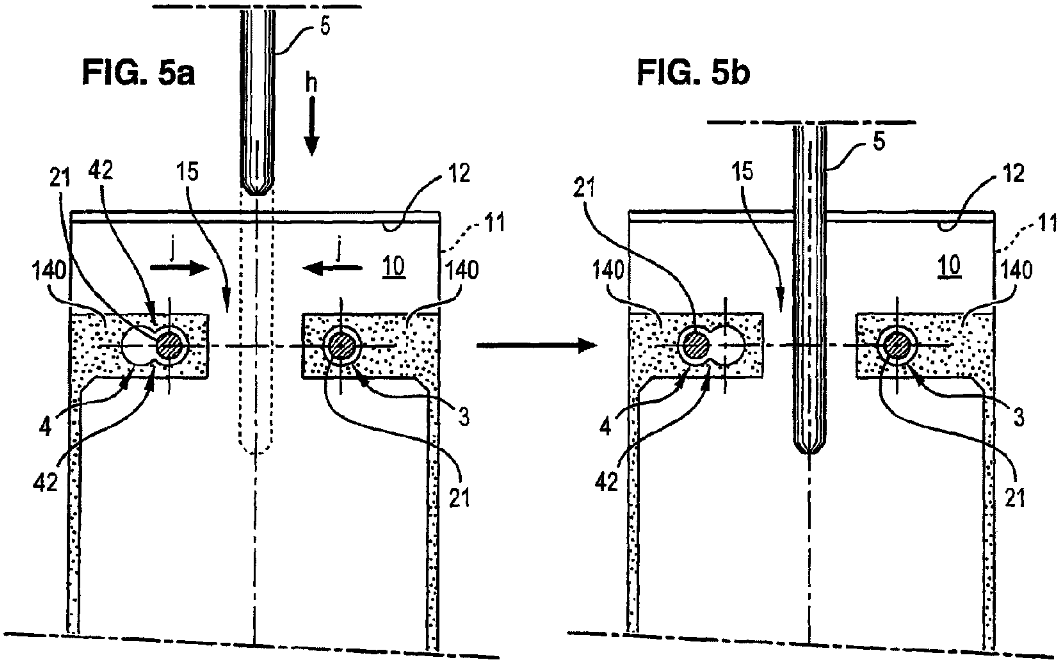
FIG. 6
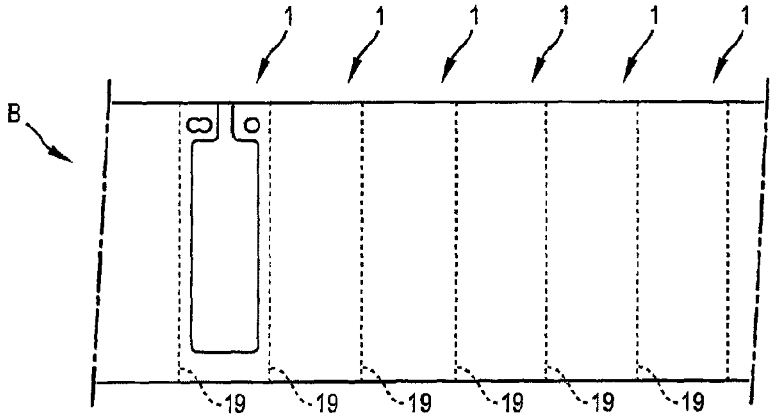

BAG FOR PACKAGING A BIOLOGICAL SUBSTANCE COMPRISING OPENINGS FOR HANGING TO A SUPPORT DEVICE, AND STRIP FORMED WITH SUCH BAGS

BACKGROUND OF THE INVENTION

1. Field of the Invention

The present invention relates to a bag for packaging a biological substance, such as animal semen.

It also relates to a strip formed by juxtaposing such bags, as well as an assembly comprised of a bag and a hooking or hanging support.

The term "biological substance" means any substance totally or partially of human or animal origin, presented as liquid, pasty or powdery solid form.

2. Discussion of Related Art

EP-B-1 317 224 describes a bag of abovementioned type, adapted particularly for packaging animal semen, in particular of porcine origin.

SUMMARY OF THE INVENTION

Referring to FIG. 1 of this document, it is seen that the bag comprises two circular openings on both sides of a filling line located in the upper part thereof.

These openings are able to allow hanging the bag to a hanging support, in view of its filling.

This filling can be made manually or automatically using a machine.

In order to undertake a manual filling, an empty bag is hanged to a supporting device that comprises at least one pair of substantially horizontal and parallel fingers, on which the bag is "fitted". The bag is somehow "hanged" to these fingers through said openings. As a matter of course, the opening size is dimensioned to the size of the fingers.

Filling is more generally undertaken using an automated machine, such as the one sold by the applicant under the trade mark "GTB 1000".

In view of this filling, the bags are presented in a strip form in which these bags are contiguous and integral with each other on one of their large sides.

This strip is brought step by step in front of a support device having several finger pairs, and this device is moved toward the strip, following a direction perpendicular to the plan thereof, in order that the fingers get introduced in the openings of contiguous bags.

Of course, the spacing between a determined pair of fingers is substantially equal to the pitch between openings of a same bag.

In order that this operation proceeds in the best conditions, the fingers are generally given a tapered form, in order that they are able to cooperate with the openings, even when a positioning and/or aligning defect of the strip occurs.

Despite, some extreme situations can occur, wherein the fingers are not well positioned, so that a "hanging" of the bags is not satisfying, or is not achieved.

In addition, during the filling operation of a bag, a rigid tube fed with semen is introduced between the two plastic walls constituting it, so as to get positioned in its filling line.

This tube forms an extra thickness that results in a tension in the surrounding plastic material. Because of these efforts, it tends to get deformed, in particular at the aforesaid openings. This deformation is not acceptable, because it can affect the subsequent bag welding made transversally to the filling line, in order to close it.

The present invention aims in particular to overcome these difficulties.

Thus the present invention relates to a bag for packaging a biological substance, such as animal semen, which is formed by two plastic walls assembled so as to define a pouch for receiving said substance and that comprises a line communicating with this pouch for filling the same, this bag comprising in addition at least one pair of openings located on both sides of said line, in order to get hung, via these openings, to fingers that are complementary to a supporting device.

This bag is characterized in that at least one of its openings has an oblong shape, extends perpendicularly to said line, and comprises an area forming a hard spot.

Thanks to the presence of this oblong form, implementation of the bag on the fingers of a supporting device will be facilitated. Moreover, during introduction of a filling tube, the motion "freedom" provided by this form to the bag allows to compensate the efforts to which it is submitted.

According to other advantageous and non limiting characteristics:

- the area forming a hard spot is an area wherein said opening has a reduced width;
- said opening has, in front view, the shape of two partially overlapping circles;
- the bag has an emptying line for said substance;
- said line extends, in relation to the pouch, substantially in regard to said filling line;
- a cannula is fitted in said emptying line.

The invention also relates to a strip of bags for packaging a biological substance, comprised of a juxtaposition of bags according one of the aforesaid characteristics.

It also relates to an assembly comprised of a bag according one of the aforesaid characteristics, and a hooking or hanging support for such a bag, comprising at least one pair of hanging fingers, characterized in that the relative spacing between these fingers is equal to the shortest pitch between said openings.

Others characteristics and advantages of the present invention will be apparent upon reading the following description of a preferred embodiment.

BRIEF DESCRIPTION OF THE DRAWINGS

This description will be made by reference to the attached drawings, in which:

FIGS. 5*a* and 5*b* are also partial view of the bag of FIG. 1, aiming to illustrate the phenomenon encountered when a filling tube is introduced therein for filling the pouch it contains;

FIG. 6 is a schematic front view of a strip of bags, formed by juxtaposing bags according to FIG. 1;

DESCRIPTION OF PREFERRED EMBODIMENTS

The bag shown on the attached drawings is more particularly intended to receive animal, notably porcine, semen.

Its general structure is of a known type. Incidentally, the bag 1 is formed of two plastic walls 10 and 11, having a rectangular elongated outline and a longitudinal axis X-X'.

This plastic material is preferably clear or translucent and is normally made of polyethylene, polyamide or polyethylene terephthalate (PET).

These two walls are preferably comprised of two distinct sheets. It is however possible to use one same sheet that will be refolded on same.

Each sheet can be single-ply or multi-ply.

Figure 1:
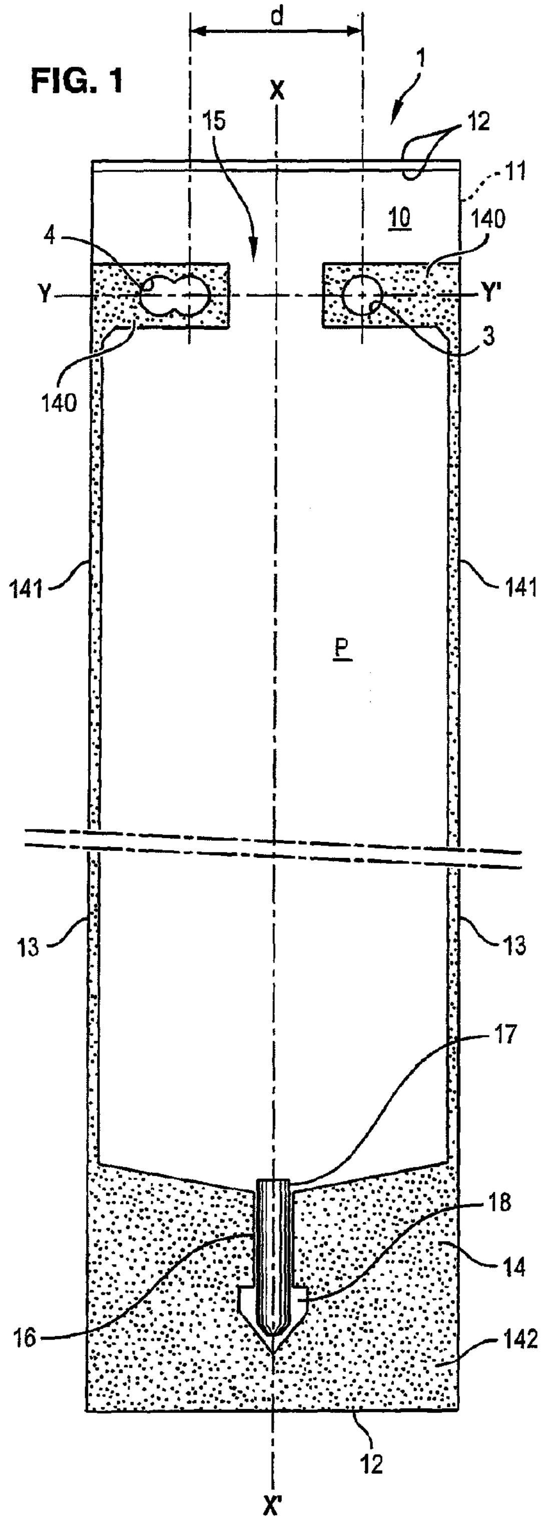
FIG. 1 is a front view of a bag according to the invention.

On FIG. 1, the longitudinal sides (parallel to the X-X' axis) of the sheets are referenced 13, whereas its small transversal sides are referenced 12. It should be noted that the sheet 11 is slightly longer than the sheet 10, so that the upper rear side 12 slightly goes past the front side. This makes easier to open the bag by slightly moving aside the sheets, in particular in order to accede to a filling line that will be described later.

The walls are joined side by side to each other in order to delineate in particular a pouch P for receiving the substance. In this example, the walls are joined side by side by welding. However, in an alternative embodiment, another technique might be used, notably by gluing.

Areas in which the walls are joined side by side are given the general reference 14 and are identified by black spots on the figures.

In the embodiment of FIG. 1, these areas 14 comprise, in the upper part of the bag, two large regions 140 having a generally rectangular shape, located symmetrically on both sides of the longitudinal central axis X-X'. A non welded area 15 extends between them and forms a line for filling the pouch P with semen.

These regions are provided with openings 3 and 4 to which we will return thereafter.

The regions 140 continue downwardly of the bag with a welding line 141 having a small width, that extends near and parallel to each of the large sides 13 of the bag. Each of these lines is connected, on the lower part of the bag, with a large region 142 having an approximately rectangular shape.

A non welded area 16 extends according to the X-X' axis and communicating with the bottom of the pouch P, which delineates an emptying line for the pouch P.

A cannula 17 is fitted in a well known manner, notably force-fitted, in this line.

An additional non welded area 18 also extends down of the line 16, which communicates directly with the lower opening of the cannula 17, notably in order to facilitate is access.

As it has been said above, the regions 140 have openings 3 and 4.

These openings allow hooking or hanging the bag to a support, particularly for its filling.

Figure 2:
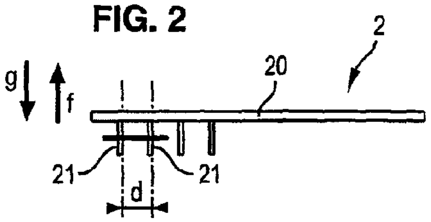
FIG. 2 is a diagram aiming to illustrate the principle of hanging a bag on a support device.

In FIG. 2 is shown very schematically an example of such a support 2, viewed from above. It comprises an elongated body 20 from which extend, in the same direction, fingers 21 for hanging a bag, of circular cross-section.

The pitch between two fingers, referenced d on FIG. 2, corresponds to the smallest pitch between the openings 3 and 4, as it can be seen on FIG. 1.

In the presently shown case, the opening 3 is circular and has a diameter corresponding substantially, give or take the clearance, to the most important diameter of each of the fingers 21.

According to the invention, the second opening 4 is comprised of an oblong shaped hole (that can also be called a port), the great axis Y-Y' of which being directed transversally, i.e. perpendicular to the X-X' axis.

The term "oblong" qualifies a shape which has a longitudinal span bigger than its transversal span.

In the embodiment of FIG. 1, the opening 4 is made by punching one of the regions 140 of the bag 1, by means of a punch having a circular outline, and this punching is made twice consecutively, so that the second punching partially covers the print surface of the first punch. It is hereby attained a shape that resembles to the numeral "8".

Figure 3A:
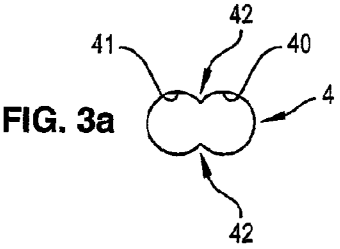
FIGS. 3*a* and 3*b* are front views of two embodiments of an oblong hole that has the bag of the invention.

This configuration can be more particularly seen on FIG. 3*a*, where the circular outlines for each "portion" of the opening 4 are referenced 40 and 41.

Reference 42 is given to protruding parts that extend in the intermediate area of the opening, having a width smaller than the largest area of each of the parts 40, 41. These protruding parts 42, as it will be indicated further, realize and constitute a "hard point" at this opening 4.

The pitch d, mentioned before, consequently corresponds to the distance between the axis of the opening 3 and the axis of the opening 4 at the part 40 that is nearest to the X-X' axis.

Returning to FIG. 2, and in case of a manual filling of the bag 1, it is common to manually position a bag by taking it in hands and by aligning the openings of the bag 1 with the fingers 21 of the support 2. This operation is shown by an arrow g in the figure. In an alternate embodiment in which this positioning is automated, the bag is part of a strip of juxtaposed bags, which strip scrolls step by step in front of a support 2 that is made to cooperate with one of the bags, by moving in the direction of the arrow f.

In the event that the support and/or the bag are poorly positioned, it is therefore possible that the fingers are not strictly against the openings 3 and 4.

Figure 4:
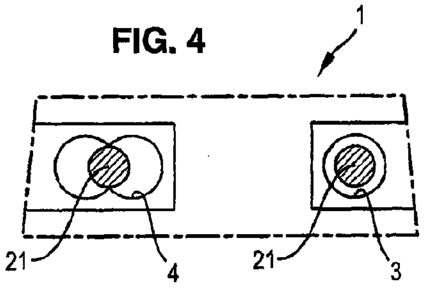
FIG. 4 is a partial view of the bag of FIG. 1, aiming to illustrate how it cooperates with the fingers of a support device.

However, according to the present invention and as it is shown in FIG. 4, the oblong shape of the opening 4 helps to overcome this difficulty insofar as there is an additional space (in this case, the part 41) for a perfect cooperation between the finger 21 of the support and this opening.

In other words, the oblong shape of the opening gives some latitude in setting up the bag on the support.

Figure 3B:
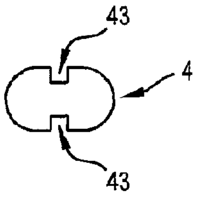

The embodiment of FIG. 3*b* differs from the latter only in that it includes two tabs 43 coming from material 43 of the rest of the bag, facing each other and at half-length of the opening 4.

In these embodiments, both in FIG. 3*a* and in FIG. 3*b*, the areas, protruding parts or intermediate tabs of the opening 4, that provide a reduced width to this opening, form a hard point area which prevents the bag to be easily moved in translation, when this is not desirable.

In other words, the "latitude" of movement provided by the opening 4 is really used only when it is necessary.

The operation of introducing a tube 5 in view to fill the bag is shown in FIGS. 5*a* and 5*b* as two separate steps.

This tube 5 is connected to a storage vial, not represented, and also to a pump, for example of a peristaltic type.

In view of filling, the tube 5 is moved in the direction of arrow h in order to get introduced between the sheets 10 and 11, opposite to the filling line 15.

Filling is then performed while the tube is in the position of FIG. 5.

Because the two sheets 10 and 11 of the bag are made from a generally rigid material and, moreover, are integral to each other in many places, introducing the tube 5, constituting an extra thickness, leads to put the bag under pressure. This results in strain areas shown by the two arrows j.

However, thanks to the presence of the oblong shaped opening 4, this phenomenon is limited or even reduced, because this strain is compensated by a sliding of the opening 4 in question, alongside the associated finger 21. FIG. 5*b* shows an extreme position of the finger 21, in which tensions have been compensated by moving the opening 4.

Closure of the bag after filling, which is made by transversally welding at the line 15, can then be realized in best conditions.

FIG. 6 shows very schematically a strip of bags B comprised by a juxtaposition of bags 1 as the one shown in FIG. 1.

These bags are integral to each other following a connecting line 19 having a low mechanical resistance, that constitutes the area corresponding to one of the longitudinal edges 15 of each bag.

Figure 7:
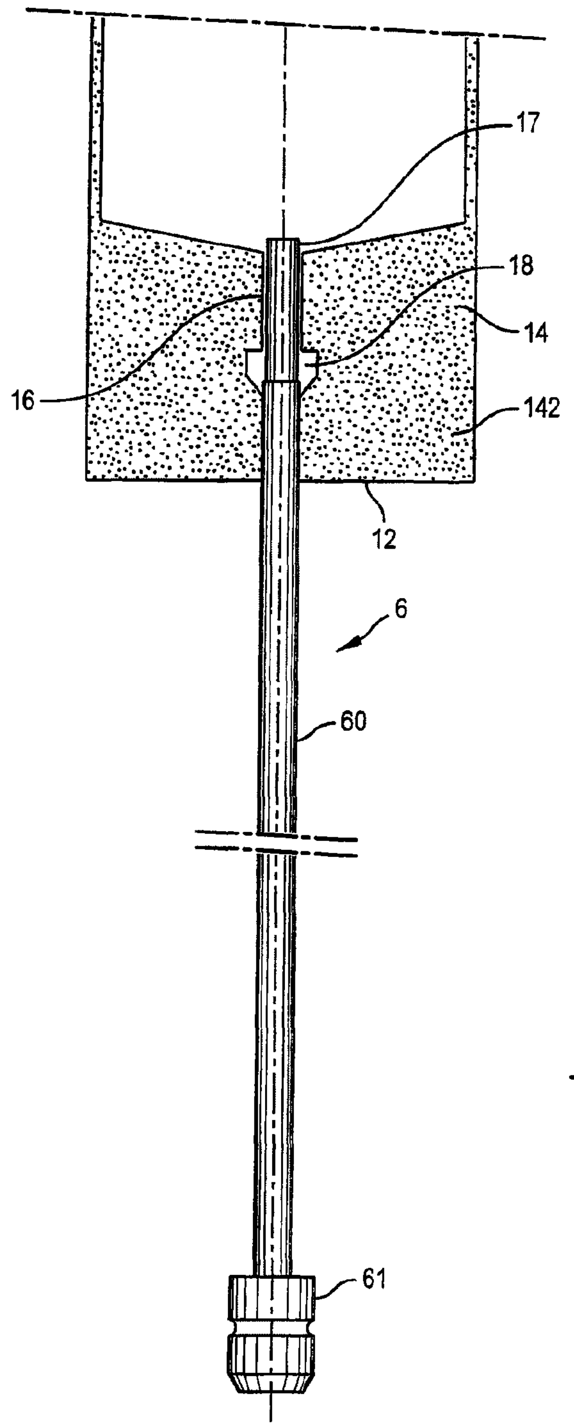
FIG. 7 is a partial front view of a bag according to the invention, connected to an insemination probe.

FIG. 7 shows partially a bag 1, filled with semen and connected to an insemination probe for porcine.

This probe, referenced 6, includes a semi-rigid plastic tube 60 having, at one of its ends, a pad 61 made from a foamy material.

This is a structure generally known by itself.

In order to connect the probe to the bag, in view to inseminate a sow, the bag is opened in order to relieve the lower end of the cannula 17 and the probe 6 is connected to the cannula 17, through the end of the tube 60 opposed to the pad 61.

The semen then flows by gravity from the pouch P to the probe 6.

Figure 8:
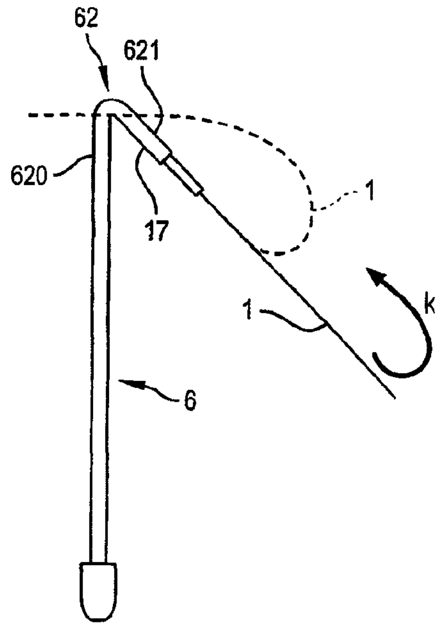
FIG. 8 is a scheme aiming to illustrate how, during an insemination, the bag is used to secure the probe in a bended position.
Figure 9:
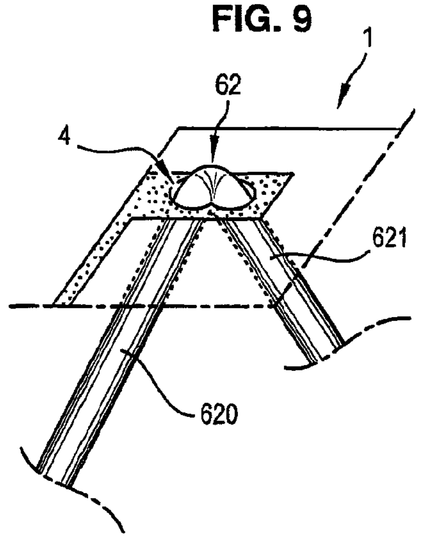
FIG. 9 is a detailed view showing the cooperating area between the probe in a bended position and the bag.

In order to avoid any semen backflow, it is relatively common that a technician performing the insemination bends the probe 6 in a marked area 62 in FIG. 8. This bending delimits a part 620 of the tube that communicates with the pad 61, and also a second part 621 that is connected to the bag.

When this bending is made, the tube unfortunately tends to naturally go back to its starting position, in which both parts 620 and 621 communicate freely. In order to avoid this, the inseminator is constantly required to keep the probe in a folded position, using one of its hands.

According to the invention, he can, by taking the bag 1 and by turning it on itself in the direction of arrow k, position the oblong opening 4 next to the bended area 62 in order that it comes to embrace this bended area.

By slightly forcing the bag in this region, the opening 4 gets strained and hugs tightly the bended area, and, as a result, the probe is fatally locked in this position.

In an embodiment not represented, the bag 1 could include not one, but two oblong openings.

Also, the invention applies to any packaging bag, presenting or not an emptying line distinct from the filling line.

French Patent Reference 08 55292, filed 31 Jul. 2008, the priority document corresponding to this invention, to which a foreign priority benefit is claimed under Title 35, United States Code, Section 119, and its entire teachings are incorporated, by reference, into this specification.

The invention claimed is:

1. A bag for packaging a biological substance, such as animal semen, which is formed by two plastic walls assembled so as to define a pouch for receiving said substance and that comprises a line communicating with said pouch for filling the same, this bag comprising in addition at least one pair of first and second openings located on both sides of said line, in order to get hung, via these openings, to respective first and second spaced apart fingers that are complementary to a supporting device, wherein said first and second openings define a shortest pitch therebetween corresponding to a spacing between said first and second fingers, wherein at least said first opening is continuously open about its periphery, has an oblong shape, that extends perpendicularly to said line for a length greater than a width of said respective first finger to permit transverse movement of said first finger relative to said first opening, and said first opening having an area of reduced width forming a hard spot, including tabs facing each other and said second opening has a shape different than said first opening.

2. The bag according to claim 1, wherein said first opening has, in front view, the shape of two partially overlapping circles.

3. The bag according to claim 1, which has an emptying line for said substance.

4. The bag according to claim 3, wherein said emptying line extends, relatively to the pouch, substantially in regard to said filling line.

5. The bag according to claim 3, wherein a cannula is fitted in said emptying line.

6. A strip of bags for packaging a biological substance, formed by juxtaposing a plurality of the bags according to claim 1.

7. An assembly comprising:

a bag for packaging a biological substance, the bag formed by two plastic walls assembled to define a pouch for receiving said substance and comprising a line communicating with said pouch for filling the same, this bag comprising at least one pair of first and second openings located on both sides of said line, in order to get hung, via these openings, to respective first and second spaced apart fingers that are complementary to a supporting device, wherein said first opening has an oblong shape, that extends perpendicularly to said line for a length greater than a width of said respective first finger to permit transverse movement of said first finger relative to said first opening, said first opening having an area of reduced width forming a hard spot, including tabs facing each other and the second of the openings is circular and a hooking or hanging support for the bag, the support comprising at least a pair of hanging fingers, wherein the relative spacing between the fingers is equal to the shortest pitch between said openings.

8. The assembly according to claim 7, wherein in a plane of said first opening having an oblong shape, said first opening having an oblong shape is moveable relative to an associated finger to allow for compensation of strain on the bag.

9. A bag for packaging a biological substance, such as animal semen, which is formed by two plastic walls assembled so as to define a pouch for receiving said substance and that comprises a line communicating with said pouch for filling the same, this bag comprising in addition at least one pair of first and second openings located on both sides of said line, in order to get hung, via these openings, to respective first and second spaced apart fingers that are complementary to a supporting device, wherein said first and second openings define a shortest pitch therebetween corresponding to a spacing between said first and second fingers, wherein at least said first opening has an oblong shape, that extends perpendicularly to said line for a length greater than a width of said respective first finger to permit transverse movement of said first finger relative to said first opening, and a pair of protruding tabs that face each other and extend into said first opening to provide an area of reduced width forming a hard spot and said second opening has a shape different than said first opening.

* * * * *